United States Patent [19]
Zor et al.

[11] 4,024,279
[45] May 17, 1977

[54] TREATMENT OF DYSMENORRHEA AND MIGRAINE SYMPTOMS

[75] Inventors: Uriel Zor; Hans Rudolph Lindner, both of Rehovot; Arie Schwartz, Tel-Aviv, all of Israel

[73] Assignee: Yeda Research and Development Company Ltd., Rehovot, Israel

[22] Filed: July 24, 1975

[21] Appl. No.: 598,807

[30] Foreign Application Priority Data

July 26, 1974 Israel .................................... 45357

[52] U.S. Cl. .............................................. 424/319
[51] Int. Cl.² ...................................... A61K 31/195
[58] Field of Search ...................................... 424/319

[56] References Cited
OTHER PUBLICATIONS

Ryan et al., Chem. Abst., vol. 81, (1974), 9983c.
Hirose et al., Chem. Abst., vol. 77, (1972), p. 87y.

*Primary Examiner*—Sam Rosen
*Attorney, Agent, or Firm*—Browdy and Neimark

[57] ABSTRACT

A pharmaceutical composition for the treatment of, or for the alleviation of primary dysmenorrhea, for the treatment of acute migraine and for attaining the relaxation of smooth muscle, and a process for the treatment of the above afflictions, comprising as active ingredient a pharmaceutically active dosage of an inhibitor of prostaglandin synthetase and action. The active ingredient of choice is flufenamic acid, meferamic acid, meclofenamic acid or niflumic acid.

2 Claims, No Drawings

TREATMENT OF DYSMENORRHEA AND MIGRAINE SYMPTOMS

Primary dysmenorrhea is one of the commonest gynecological complaints and represents a major cause of lost working and school days, yet it is pathogenesis remains obscure. No consistently effective treatment has been devised, other than the continued use of antiovulatory oral contraceptives, a choice that is not always acceptable. Another common disorder is migraine. Migraine attacks can be very severe, and are often associated with visual and gastro-intestinal disturbances.

We adopted as our working hypothesis that prostaglandins probably play a significant role in the causation of these syndromes. An early pointer in this direction was the demonstration by Clitheroe et al., J. Phys. 156 (1961) 225-237, of smooth muscle stimulants in menstrual fluid, later identified as prostaglandins. Recently, it was found that the $E_2$ and $F_2 \alpha$ level of prostaglandin in human endometrium is high at menstruation, Dounie et al, J. Phys. 236 (1974) 465-472. Studies by the inventors showed that both prostaglandin synthetase activity and the concentration of prostaglandins in the rat endometrium increase strikingly during the development of a deciduoma, Lindner et al, Proc. Roy. Soc. Med.-N.Y., (1973) in press. The appearance of an extensive decidualized layer in the subepithelial stroma is believed to be a regular feature of the human endometrium during the last few days preceding menstruation. Excessive release of prostaglandins during menstrual breakdown of this decidual tissue, together with sensitization of the myometrium to the oxytocic action of prostaglandin by the attendent cesssation of progesterone secretion, could conceivably lead to painful uterine contractures. Massive absorption of prostaglandins into the circulation could also account for the diarrhea and cardiovascular symptoms that are commonly associated with dysmenorrhea. The following results of clinical tests indicate that the treatments according to the present invention afford relief in a large percentage of patients suffering from the above afflictions.

The studies of Vane, see Nature, 231 (1971) 232-235, established that a wide range of non-steroidal anti-inflammatory and antipyretic drugs, such as indomethacin, aspirin and the fenamates, are potent inhibitors of prostaglandin synthetase. The fenamates are peculiar in that they inhibit not only prostaglandin synthetase, but also the action of exogenous prostaglandin on bronchial smooth muscle contraction, Collier et al, Nature 219 (1968) 864-865, uterine tubal contraction, Levy et al, Br. F. Pharm. 43 (1971) 236-241, and ovarian cyclic AMP and progesterone formation. We therefore examined the effects of treatment with various fenamates such as flufenamic acid (N-($\alpha,\alpha,\alpha$-trifluoro-m-tolyl)anthranilic acid), mefenamic acid, meclofenamic acid and also with niflumic acid, on subjects suffering from severe primary dysmenorrhea and from migraine attacks. The daily dosage varied from about 0.1 gram to about 1.2 gram. Similar considerations led us to believe that a substantial relief or migraine attacks can be obtained with the above drugs.

A. Flufenamic Acid: Patients and Treatments

Thirty women with recurrent severe dysmenorrhea were included in the trial, Twenty five of these were nulligravidae, 18-22 years of age. The remaining five patients were 25 -35 years old; one nulligravida and four with a history of 1-2 normal deliveries and 1-2 artificial abortions each. The symptoms complained of were nausea, diarrhea, vomitting, dizziness, abdominal and/or lower back pain, headache and premenstrual tension. The duration of dysmenorrhea ranged from 2-4 days. Thorough gynecological examination of the patients revealed no organic cause of the dysmenorrhea such as inflammation of pelvic organs, endometriosis or neoplasia. None of the patients had a history of peptic ulcer. Flufenamic acid (Flunalgan, Rafa Laboratories Ltd. Jerusalem) was given per os starting on the first day of menstrual flow at the dose level of 125 mg four times a day, followed by 125 mg three times a day on the two or three subsequent days. Control cycles were treated with non-morphine analgesics, spasmolytics, tranquilizers or with a placebo (vitamin pill). Three women had previously been treated with oral contraceptives (Metrulen-M, Searle, containing 1 mg ethynodiol diacetate and 0.1 mg mestranol, or Gynovlar 21, Schering AG, containing 3 mg norethisterone acetate and 0.05 mg ethinyl estradiol) for 21 days starting 5 days after the beginning of menstrual flow. Assessment of the results was based on the subjective feeling of the patients as reported to the physician.

RESULTS

Treatment with flufenamic acid abolished the symptoms of dysmenorrhea in all 30 patients in 70 of 70 treated cycles, except that in two patients mild nausea persisted, unaccompanied by vomitting or pain, and one patient continued to complain about dizziness, but was relieved of all other symptoms (nausea and diarrhea). All 30 patients continued to have normal cycles during and following treatment with flufenamic acid, but the symptoms of dysmenorrhea reappeared when medication was withheld. Treatment of the same group of patients with a placebo (5 patients), non-morphine analgesics (9 patients), spasmolytics (2 patients) or tranquilizers (3 patients) afforded no significant relief in 72 of 72 cycles. Four patients treated with oral contraceptives experienced complete remission of symptoms, but these recurred on cessation of treatment.

In a manner similar to that of the above experiments with flufenamic acid, experiments were carried out with the other compounds listed above. Experiments were first carried out with rats and rabbits and these showed mefenamic acid and meclofenamic acid to be even slightly more effective than flufenamic acid in the inhibition on prostaglandin formation and its biological activity. Niflumic acid was slightly less active. Some experiments were carred out with patients suffering from primary dysmenorrhea and the results indicate an activity similar to that of flufenamic acid.

A further experiment was carried out with a group of 40 young women (18 to 35 years of age), suffering from severe primary dysmenorrhea. They were treated with flufenamic acid, 125 mg t.i.d. or q.i.d., during 1 to 3 menstrual periods. In all the patients, a total of 90 menstrual cycles, the drug afforded symptomatic relief. Treatment with analgesics, with spasmolytic, with tranquilizing drugs and also with placebos, was ineffective with these patients (a total of 72 control cycles). Flufenamic acid inhibits prostaglandin synthetase and the biological activity of prostaglandin $F_2 \alpha$ on smooth muscle. The drug brings about a relaxation of smooth muscles.

Thirty patients suffering from migraine attacks were treated for a period of 3–16 months with flufenamic acid (125 mg × 3–6/attack), an inhibitor of prostaglandin synthetase and action. In all patients (a total of 250 treated attacks), the drug afforded symptomatic relief. Side effects observed were mild dyspepsia (8 patients). None of eight patients treated with placebo reported any relief (20 attacks). The "common" anti-migraine drugs afforded symptomatic relief in twelve of the patients, partial relief in seven, and no relief in seven cases. The treatment with flufenamic acid was based on the suggestion that prostaglandins are involved in migraine attack, and that the drug relieves migraine by inhibition of the vasodilatatory action of prostaglandins. Similar effects can be obtained with the other drugs mentioned above, i.e., mefenamic acid, meclofenamic acid and niflumic acid. The drugs act also as effective relaxants of smooth muscle.

We claim:
1. A process of treating or alleviating the symptoms of primary dysmenorrhea, including diarrhea, in mammals, comprising administering an effective quantity of flufenamic acid, mefenamic acid or meclofenamic acid.
2. A process of treating or alleviating the symptoms of migraine attacks, in mammals, comprising administering an effective quantity of flufenamic acid, mefenamic acid or meclofenamic acid.

* * * * *